United States Patent [19]

Fossati et al.

[11] Patent Number: 5,017,498
[45] Date of Patent: May 21, 1991

[54] INDICATOR COMPOUNDS, METHOD OF THEIR PREPARATION AND USE OF THOSE COMPOUNDS IN AN IRON ASSAY SYSTEM

[75] Inventors: Piero Fossati, Lissone, Italy; Holger Heidenreich, Kuden, Fed. Rep. of Germany; Herbert Hugl, Gladbach, Fed. Rep. of Germany; Klaus Wehling, Wuppertal, Fed. Rep. of Germany

[73] Assignee: Miles Inc., Elkhart, Ind.

[21] Appl. No.: 317,450

[22] Filed: Mar. 1, 1989

[30] Foreign Application Priority Data

Mar. 3, 1988 [IT] Italy .................. 47682 A/88

[51] Int. Cl.⁵ .................................. G01N 33/20
[52] U.S. Cl. .......................... 436/84; 544/182; 436/63; 436/74; 436/910
[58] Field of Search ............ 544/182; 436/63, 74, 436/84, 910

[56] References Cited

U.S. PATENT DOCUMENTS 3,836,331 9/1974 Stookey ..................... 436/84
4,308,027 12/1981 Ceriotti ..................... 436/74
4,588,695 5/1986 Takano et al. .............. 436/84

Primary Examiner—Robert J. Warden
Assistant Examiner—Lyle Alfandary Alexander
Attorney, Agent, or Firm—Roger N. Coe

[57] ABSTRACT

The present invention is related to compounds of the general formula (I)

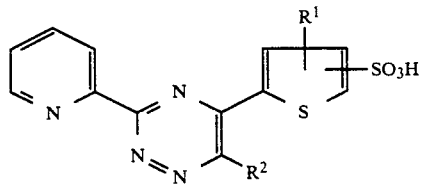

wherein
R¹ denotes hydrogen, halogen or $C_1$–$C_4$ alkyl and
R² denotes $C_1$–$C_4$ alkyl, aryl or heteroaryl, or a substituted $C_1$–$C_4$ alkyl, aryl or heteroaryl and their preparation. The compounds can be used in an iron assay system.

5 Claims, 5 Drawing Sheets

INDICATOR COMPOUNDS, METHOD OF THEIR PREPARATION AND USE OF THOSE COMPOUNDS IN AN IRON ASSAY SYSTEM

SUMMARY OF THE INVENTION

The present invention is related to compounds of the general formula (I)

wherein
R[1] denotes hydrogen, halogen or $C_1$–$C_4$ alkyl and
R[2] denotes $C_1$–$C_4$ alkyl, aryl or heteroaryl, or a substituted $C_1$–$C_4$ alkyl, aryl or heteroaryl, and their preparation. The compounds can be used in an iron assay system.

Alterations of iron metabolism reveal themselves both as deficiency diseases and overload diseases of the element. Iron deficiency diseases are widely diffused and also affect populations of highly developed countries besides obviously underfed people. Iron deficiency anemia preferentially affects women for increased iron losses with menstruation, pregnant women for increased iron needs, patients with ulcer or other causes of acute or chronic bleeding. Also neonates are particularly exposed to the disease.

The diagnosis of iron deficiencies, their differentiation from low blood iron during phlogistic diseases, and the monitoring of therapy, require accurate and reproducible laboratory tests.

The laboratory diagnosis in this field takes advantage essentially of the measurements of:
blood iron
blood transferrin
blood ferritin
globular volume and hemoglobin
free erythrocyte protoporphyrin.

While all the other tests are largely established in the clinical laboratory, the free erythrocyte protoporphyrin assay is now emerging from the "experimental incubation" phase for the clinical routine application.

The term blood iron refers to the level of iron actually transported in the plasma and consequently bound to transferrin. Although it is not a sure index of the iron content of the body, the blood iron assay is valuable to estimate the status of the amount of stored iron. Major causes that can lead to an iron deficiency or surplus are shown in Table I.

TABLE I

| Causes of Variation of Blood Iron |
|---|
| CAUSES OF DECREASE |
| Insufficient intake of dietary iron |
| (babies, vegetarians) |
| Defective absorption |
| (total and subtotal gastrectomy, achlorhydria, chronic diarrhoea and steatorrhoea) |
| Prolonged blood losses |
| (chronic hemorrhage due to gastric, duodenal ulcer, etc.) |
| Increased needs |
| (pregnancy, lactation) |

TABLE I-continued

| Causes of Variation of Blood Iron |
|---|
| Iron storage in the cells of the RE system |
| (chronic or other infections) |
| CAUSES OF INCREASE |
| Increased degradation of erythrocytes |
| (Hemolytic anemia, autoanticorpal anemia) |
| Disorders of hemoglobin synthesis |
| (pernicious anemia, sideroachrestic anaemia) |
| Acute liver diseases |
| (viral hepatitis, toxic hepatitis) |
| Hemosiderosis |
| Hemochromatosis |

Iron deficiency generally evolves through various phases slowly before resulting in frank anemia. It should be noted that a low blood iron level does not necessarily reflect the existence of a status of iron deficiency. Blood iron in addition deviates markedly from normality only when the variations of the status of saturation of the amount of stored iron have become significant.

The blood iron is A quite variable parameter. It presents marked and well known fluctuations both within-a-day and between-days.

Various authors have documented the existence of a circadian rhythm of blood iron, with a peak in the morning between 8 and 10 and lower values in the late afternoon. Particularly interesting is that, in subject working at night, the more elevated values are shifted in the afternoon, in phase with the cycle-sleep-activity; consequently the rhythm appears to be reversed.

The reference intervals reported in the literature are also different; the normal values are, among other things, influenced by physiological factors such as age (higher values in the neonate and lower values in the elderly) and sex (slightly high values in men).

The biological variability of blood iron and the possibility of increases for cellular necrosis processes (for example acute liver diseases) and decreases for phlogistic conditions (because of the bond with transferrin) limit the diagnostic value of the measurement.

For more detailed information reference is made, for example, to "Iron Clinical Significance and Methods of Assay" a publication of July 1986 edited by Ames Division, Miles Italiana S.p.A.

The most serious problem of iron testing is the low concentration of the analyte especially in case of a decrease. Further the tight bond between the iron and the transferrin requires drastic reaction conditions (in the assay system) to release the iron from this transport protein. Interference caused, for example, by copper is a serious problem, too.

The present invention now provides new compounds which are very useful as indicator compounds in an iron assay system. The complex of iron with the present compounds not only show a high sensitivity but also a very high stability at lower pH-ranges. The stability of the iron-indicator complex at lower pH is very desirable, because this allows less drastic conditions for the promotion of the release of iron from the transport of the protein transferrin.

The present invention concerns compounds of the general formula (I)

[Structure (I): pyridine-N=C-N=N with R¹-substituted thienyl-SO₃H and R² groups]

wherein

R¹ denotes hydrogen, halogen or alkyl and

R² denotes $C_1$-$C_4$ alkyl, aryl or heteroaryl or a substituted $C_1$-$C_4$ alkyl, aryl or heteroaryl.

Preferred are compounds of formula (I) wherein

R¹ denotes hydrogen and

R² denotes $C_1$-$C_4$ alkyl, aryl or thienyl, which radicals can be substituted by $C_1$-$C_4$ alkyl, hydrogen, halogen or $SO_3H$.

More preferred are compounds of formula (I) wherein

R¹ denotes hydrogen and

R² denotes methyl, ethyl, propyl, phenyl, tolyl or thienyl.

In particular the present invention concerns compounds of formula (I) wherein

R₁ denotes hydrogen and

R₂ denotes

[phenyl group with R¹¹ substituent]

wherein

R¹¹ denotes hydrogen, methyl or chlorine.

The most preferred compound is a compound having the formula

[Structure: pyridine-N=C-N=N with two thienyl-SO₃H groups]

The present invention is further related to an assay system for detection or quantitative determination of iron in a sample comprising one of the compounds.

In a preferred embodiment the iron assay system further comprises a reducing compound of the formula

[Structure: tetrahydrobenzo(h)quinoline with HN and OH groups]

Consequently the present invention is also related to the use of this compound in the determination of iron. The mentioned quinoline compound has been determined as very useful for the reduction of $Fe^{3+}$ to $Fe^{2+}$, which is necessary in the iron test system. Ascorbic acid or other reducing agents known in the art can also be used in connection with the new indicators of the present invention, but the above quinoline compound is preferred for the purpose of reduction. Consequently, the present invention is also related to the use of 3-hydroxy-1,2,3,4-tetra-hydro-benzo(h)-quinoline as reducing agent in an assay system for the determination of iron.

The iron assay-system can furthermore contain substances which do not react, such as, for example, buffers, wetting agents, stabilizers and the like.

Reagent combinations can be prepared from the above compounds. The reagent combination can be in the form of a solution or as a powder or are in the form of tablets or a lyophylisate. The reagent combination (if it is not already in the form of a solution) is taken up in water or another suitable solvent and a reagent solution is prepared. If the reagent combination consists of individual components, these are to be mixed with one another. After the sample (for example blood, serum, plasma or urine) has been mixed with an aliquot portion of the reagent mixture, the color formed is measured on a photometer and the concentration of iron is calculated via the molar extinction coefficient and the volumes of reagent and sample added, or via an iron standard aqueous solution.

The iron assay system can furthermore be impregnated, together with a buffer system, with appropriate wetting agents and activators as well as other auxiliaries, onto absorbent reagent carriers, such as papers, fleeces and the like. For this, one or more impregnating solutions can be prepared in the form of aqueous, organic or mixed solutions, depending on how the reagents or auxiliaries dissolve. Absorbent or swellable carriers, preferably filter paper or absorbent fleece of glass or plastic, are impregnated or sprayed with these solutions. The carriers are then dried. The reagent carriers thus prepared can be used either as rapid diagnostics for direct determination of the contents of the analyte in the liquid (for example in body fluids, such as blood, urine or saliva, in foodstuffs, for example fruit juices, milk and the like). The liquid is thereby applied directly to the reagent carrier or this is immersed briefly in the liquid. Semiquantitative determination is possible by allocating a comparison color to the thus formed. Quantitative evaluation can be carried out by reflectance photometry.

It is also possible to introduce the test agent according to the invention into carrier matrices prepared from casting solutions. Examples which my be mentioned here are cellulose, cellulose derivatives, gelatin, gelatin derivatives or plastics, such as polyurethanes and polyacrylamide. It is advantageous here that the test agent and if appropriate the other necessary reagents are added directly to the casting solution, which means that it is possible to produce the test device, consisting of the carrier and reagents, in one operation.

By eluting the above-mentioned reagents with water or buffer or serum from the absorbent carrier, a reagent solution can be prepared, with which the analyte or enzymes can be determined in the cell of a photometer as described above.

Wetting agents are, in particular, anionic and cationic, nonionic or anphotheric wetting agents.

Other auxiliaries which my be appropriate are the customary thickeners, solubilizing agents, emulsifiers, optical brighteners, contract media and the like. such as are known in corresponding tests with other chromogens.

The preparation of the compounds according to the invention can be illustrated by way of an example:

The required starting materials are known from the literature [of for example: *Acta. Chem. Scand.*, 23, 1087 et seq (1969); *J. Amer. Chem. Soc.*, 75, 1115 (1953); Organikum, Organisch chemisches Grundpraktikum, page 325 et seq. (1970)].

DESCRIPTION OF THE PREFERRED EMBODIMENTS

Preparative Examples

Example 1

6.44 g (grams) of 3-(2-pyridyl)-5,6-bis(2-thienyl)-1,2,4-triazine are introduced into 25 ml (milliliter) of 25% strength oleum at 0° C. The reaction mixture is allowed to reach room temperature and is stirred further for 24 hours. The sulphonation mixture is then discharged on to ~100 g of ice, buffered with a small quantity of NaOH and the precipitate is filtered off with suction. 8.4 g of a yellow powder are isolated which forms a blue color with iron (II) ions in water ($\lambda_{max}$=593 nm; c=34000). It is clear from the NMR spectrum that the powder is one of the following possible isomers:

Example 2

The 3-(2-pyidyl)-5,6-bis (2-thienyl)-1,2,4-triazine required in Example 1 is prepared in the following manner:

13.6 g of picolineamidrazone and 22.2 g of thenil are stirred in 125 ml of ethanol at room temperature. After 24 hours the reaction mixture is concentrated in a rotary evaporator and the residue is recrystallized from absolute ethanol. C - 13 NMR data

| | |
|---|---|
| C-1 | 150.40 D |
| C-2 | 125.33 D |
| C-3 | 139.01 D |
| C-4 | 124.04 D |
| C-5 | 160.04 D |
| C-6 | 152.63 S |
| C-7 | 149.54$^a$ S |
| C-8 | *****$^a$ S |
| C-9 | 136.89 S |
| C-10 | 131.73 D |
| C-11 | 129.60 D |
| C-12 | 128.83 D |
| C-13 | 137.11 D |
| C-14 | 128.27 D |
| C-15 | 129.81 D |
| C-16 | 132.32 D |

Example 3

284 g of phosphorous pentaoxide are stirred in a mixture of 2500 ml of toluene and 250 ml of thiophene. Then 300 g tolylacetic acid are added in portions at 80° C. The mixture is subsequently stirred for 5 hours and is then discharged onto ice. The organic phase is separated off, dried and concentrated in a rotary evaporator. The residue is recrystallized from aqueous ethanol. 326 g of the following compound are obtained.

Example 4

27.75 g of selenium dioxide are suspended in a mixture of 250 ml of dioxane and 20 ml of water. 54.0 g of the thienyl ketone of Example 3 are added to this suspension and the mixture is then heated for 6 hours under reflux, filtered off by suction to remove the residue and the reaction mixture is concentrated in a rotary evaporator. 49.2 g of a brown oil of the following formula are obtained and processed further without purification.

Example 5

23.0 g of the diketone prepared in Example 4 are heated under reflux with 13.6 of picolineamidrazone in 100 ml of ethanol. The triazine formed already crystallizes out under boiling heat. After 1 hour the mixture is cooled and filtered off with suction. 33.9 g of a yellow powder with a melting point of 191° C. are isolated. The spectra do not allow the product to be assigned definitely to one or other of the following two isomers:

Example 6

If the triazine of Example 5 is reacted with 25% strength oleum according to the process described in Example 1, the monosulphonated compound is obtained which can be assigned to one of the following structures:

Calculated: C, 52.77; H, 3.03; N, 12.96; O, 11.1; S, 14.83; N, 5.31.
Found: C, 52.3; H, 3.1; N, 13.0; S, 15.0.

Example 7

If 6.44 g of 3-(2-pyridyl)-5,6-bis(2-thienyl)-1, 2,4-triazine is stirred in 50 ml of sulphonated monohydrate for 7 hours at 50° C. and the mixture is then worked up as described in Example 1, 3.2 g of the following compound, which has a melting point of higher than 250° C., are obtained:

Example 8

If pyridinylthiophene is reacted with picolineamidrazone as described in Example 5 one of the two following possible triazines are obtained in a yield of 80% [JR:1385 cm$^{-1}$ (-CH$_3$)]:

Example 9

The triazine derivative of Example 8 is sulphonated in monohydrate at a temperature of 50° C. After working up a yellow powder which corresponds to one of the following formula, is obtained in a 65% yield.

Analysis:
Calculated: C, 43.82; H, 2.55; N, 15.72; O, 13.47; S, 17.99; Na 6.45.
Found: H, 44.00; H, 2.45; S, 18.2.

Test Examples

In the following iron tests the compound of Example 1 has been used as indicator.

Principle of the Test

Iron in human serum is released from its carrier protein, transferrin, in an acid medium and simultaneously reduced to the ferrous form by a reducing agent. Ferrous ions chelate with the indicator forming a stable blue complex whose absorbance, spectrophotometrically read at 593 nm (nanometers), is proportional to the iron content. Deproteinization is not required. A sample blank is required to correct for the serum matrix effect.

MATERIALS AND METHOD

Experiments (formula optimization, linearity, comparison studies, etc.) were carried out according to the following directions:

Sample: human plasma heparinized or human sera (native or spike with ferric ions) obtained from hospital routine were used. Aqueous solutions of iron were prepared dissolving from iron metal (NBS material code 937) with nitric acid and diluting to the appropriate concentration with distilled water.

Instrumentation: a double-beam spectrophotometer (model Lambda 5, Perkin Elmer Corp.) was used.

Materials: The iron indicator was the compound of Example 1, all other compounds were reagent-grade materials. The working solution contains the buffer, the reducing agent, thiourea (to suppress a possible copper interference) and the indicator compound. A working solution without the indicator compound was also prepared for the sample blank tests. For comparison studies the SERA-PAK Iron kit, Ferene-S method of Ames Division, Miles Italiana S.p.A., was used.

Test procedure

| Wavelength | 593 nm (570-610) |
| --- | --- |
| Cuvette | 1 cm light path |
| Temperature | room temperature |
| Reading | against reagent blank for standard and sample; against distilled water |

-continued

| | for sample blank | | | |
| --- | --- | --- | --- | --- |

| | Pipette into test tubes: | | | |
| --- | --- | --- | --- | --- |
| | Reagent blank | Sample blank | Standard | Sample |
| Distilled water | 0.20 | — | — | — |
| Sample | — | 0.20 ml | — | 0.20 ml |
| Standard | — | — | 0.20 ml | — |
| Work, Solution without indicator | — | 1.00 ml | — | — |
| Work, Solution | 1.00 ml | — | 1.00 ml | 1.00 ml |

Mix and allow to stand at room temperature for 5 min. Read the absorbance of the sample blank (Asb) against distilled water and the absorbance of the sample (As) and of the standard (Ast) against the reagent blank.

Calculation:

$$\frac{As - asb}{Ast} \times \text{concn. of the standard used } (\mu g/dl) = \text{Iron in the sample } (\mu g/dl)$$

OPTIMIZATION STUDIES pH Optimization

Starting with a formulation containing the following components:

| Indicator | 3.5 mmol/L |
| --- | --- |
| Thiourea | 63 mmol/L |
| Ascorbic acid | 10 mmol/L |
| Buffer | 180 mmol/L: pH range 0.5-5.0 |

The effect of pH on the iron test was studied using 3 aqueous solutions of iron at concentrations of approximately 200, 500 and 1000 μg/dl and two different human plasma pools at approximately 300 μg/dl of iron. Different types of buffer were used to cover the pH range:

KCl/HCl for the pH 0.5-1.0-1.5-2.0

Citric acid/NaOH for the pH 2.0-2.5-3.0

Acetic acid/HaOH for the pH 3.0-4.5-5.0

Figure 1:
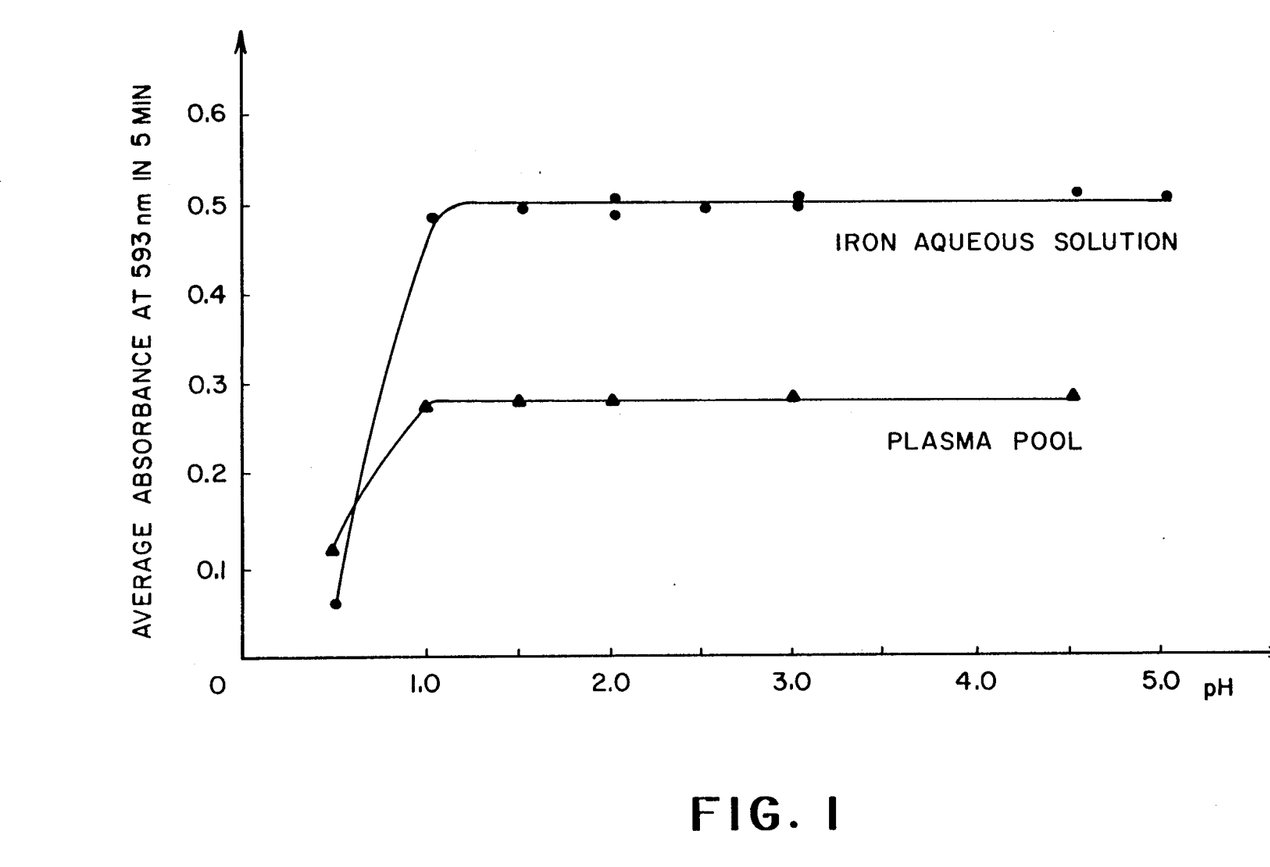
FIG. 1 shows the average absorbance of aqueous iron solutions v.s. solution pH.

Color development was monitored at 593 nm and the absorbance after 5 min. at room temperature (end-point of the reaction) was taken (see Table 1). The average absorbance for the three aqueous solutions of iron and for the two pools of plasma were calculated and plotted vs. pH (FIG. 1)

From the data it is evident that the indicator compound according to the invention can be used for pH values equal or greater than 1, and preferably of about 1 to facilitate the release of iron from transferrin.

Choice of the buffer

Compounds able to give buffer solution at pH 1 were selected; e.g. using the KCl/HCl or citric acid or malonic acid as buffer agents and testing at pH 1.0 and 0.3 mol/L aqueous solution of iron and human plasma. No difference in absorbance response and time of reaction were noticed. All the compounds tested were found to have the same buffer capacity with human sera.

Choice and Optimization of the Reducing Agent

Ascorbic acid is the reducing agent generally used to reduce ferric ions; unfortunately the compound is stable only for a few hours when it is put into solution. Consequently, in general the iron kits commercially available, supply the ascorbic acid in powder form to be added manually to a preformed solution (i.e. see Sera-Pak Iron kit). In order to obtain a ready to use solution a search was carried out to find a more stable and appropriate reducing agent. The 3-hydroxy-1,2,3,4-tetrahydro-benzo(h) quinoline (HTBQ)

was found very suitable, in an acid medium, the ascorbic acid to reduce the ferric ions to ferrous ions and to promote the iron release from transferrin.

Starting with a formulation containing the following components:

| HCl/KCl buffer pH 1.0; | 100 mmol/L |
|---|---|
| Indicator | 3.5 mmol/L |
| Thiourea | 63 mmol/L |

Figure 2:
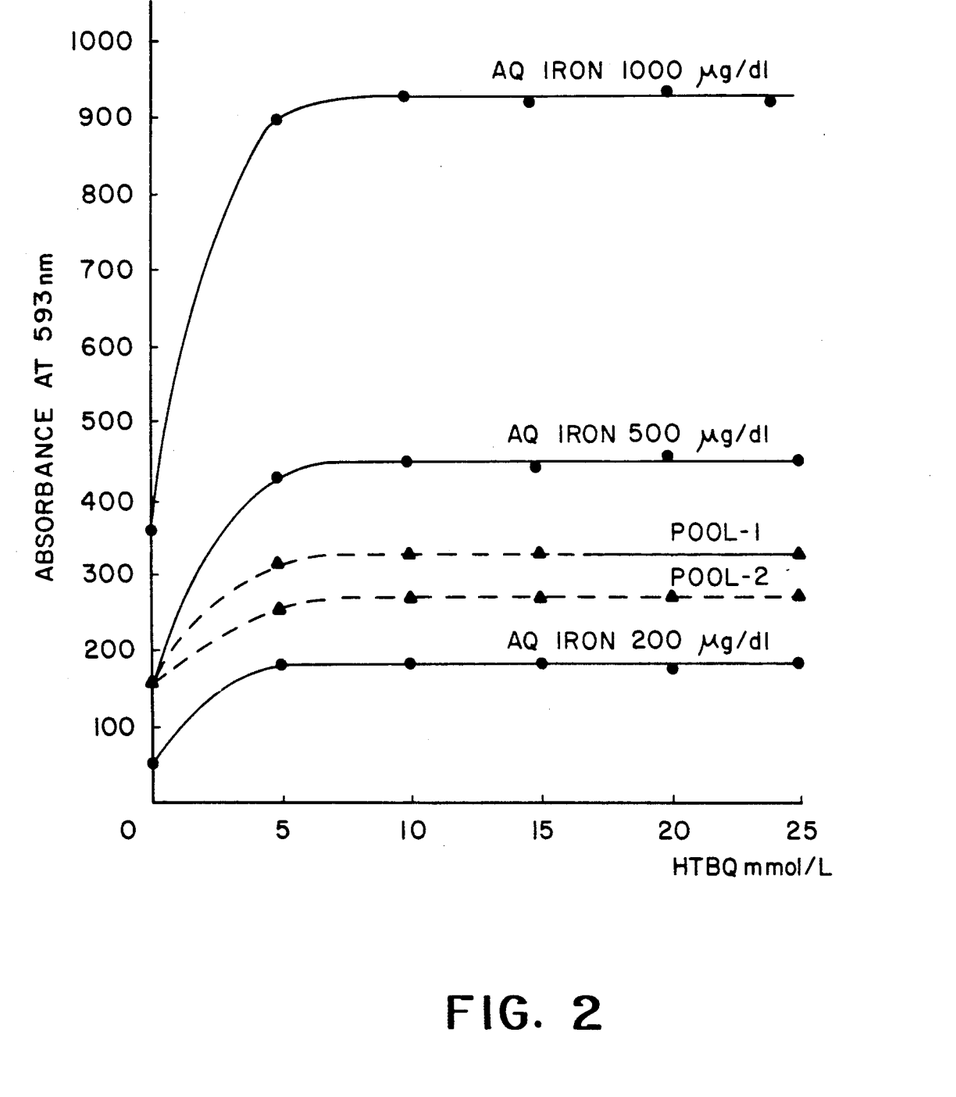
FIG. 2 shows the minimum required concentration of the present formulation.

The HTBQ was added in concentrations ranging from 0 to 25 mmol/L and the absorbance response to 593 nm after 5 min of reaction was recorded using aqueous solutions of iron and two different human plasma pools. Data in FIG. 2 show that a minimum amount of 5–10 mmol/L of HTBQ is required; a concentration of about 10 mmol/L is preferable.

Indicator Optimization

Starting with a formulation containing:

| HCl/KCl buffer pH 1.0; | 200 mmol/L |
|---|---|
| Thiourea | 63 mmol/L |
| HTBQ | 20 mmol/L |

Figure 3:
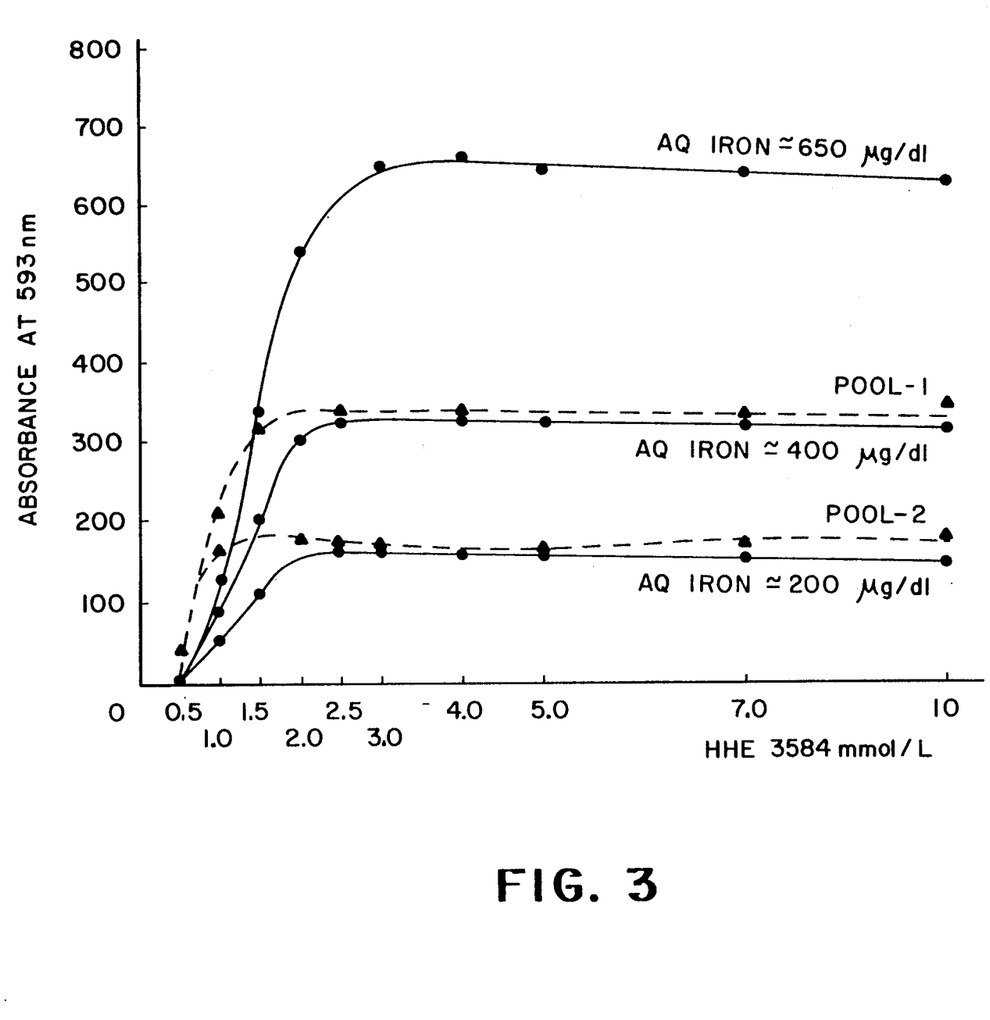
FIG. 3 shows a useful range of the present formulation.

The indicator was added in concentrations ranging from 0.5 to 10 mmol/L and the absorbance response at 593 nm after 5 min. of reaction was monitored using aqueous solutions of iron and two different pools of human plasma. Data in FIG. 3 show that a minimum amount of 2.5–3 mmol/L of the indicator is required; a concentration of about 3.5 mmol/L is preferable.

From the optimization studies carried out the following remarks can be made:

1. pH: the system works in the pH range from 1 to 5; a pH=1 is preferred to facilitate the dissociation of iron from transferrin. Choosing a pH over 3.0 it is preferable to introduce in the working solution a surfactant to avoid possible sample turbidity; Triton X-100 or Tween 10 at a concentration of 0.5% can be used. pH higher than 5 were not tested but it is presumable that the system could work if an appropriate component to dissociate iron from transferrin is used.

2. Buffer: different types of compounds can be used (e.g. citric acid, malonic acid, HCl/KCl).

3. Molarity; a buffer molarity less than 400 mmol/L and preferably of about 200 mmol/L is preferred to avoid possible human sample turbidity; however a molarity higher than 400 mmol/L can be used in appropriate surfactants are used.

4. Reducing Agent: HTBQ can conveniently substitute the ascorbic acid. A concentration above 5 mmol/L is suggested, a concentration of about 20 mmol/L is preferred.

5. Indicator Compound: a concentration above 2.5 mmol/L is suggested, a concentration of about 3,5 mmol/L is preferred.

6. Thiourea: using a formulation at pH 1.0 this component is not necessary and its use can be avoided; above this pH value a concentration of 63 mmol/L is satisfactory to suppress copper interference, (data not shown).

PERFORMANCE VALIDATION

The performance validation was carried out according to the test procedure initially reported and with formulation containing the following components:

| HCl/KCl Buffer pH 1.0; | 200 mmol/L |
|---|---|
| Indicator | 3.5 mmol/L |
| HTBQ | 20 mmol/L |

Linearity tests

Figure 4:
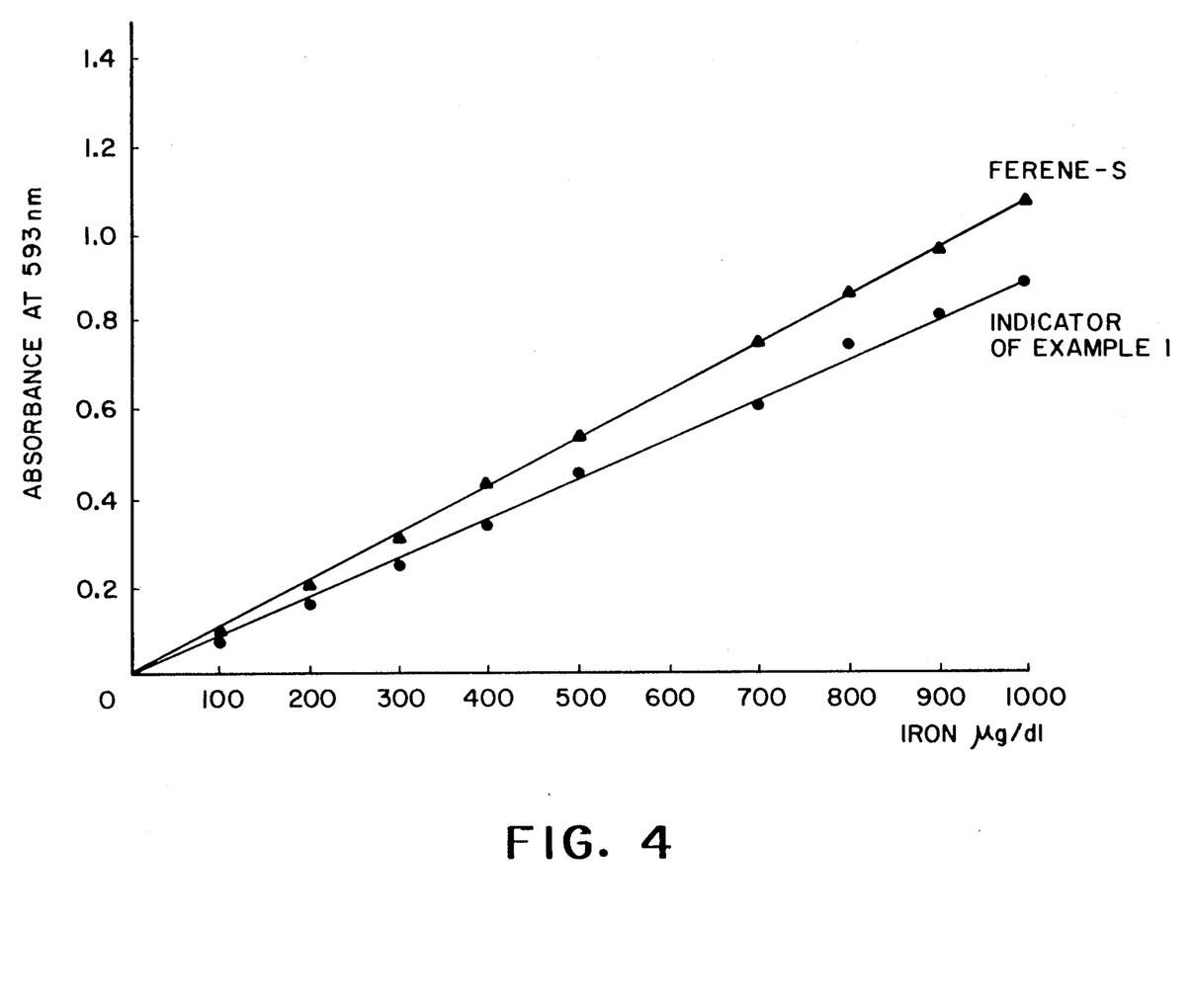
FIG. 4 shows the linear relationship of the present formulation using a NBS standard up to a concentration of 1000 μg/dl of iron.

Aqueous standards of ferric ions, prepared by dissolving iron metal (NBS material) in nitric acid and diluted to appropriate concentrations with distilled water, were assayed in triplicate. FIG. 4 shows a linearity up to at least 1000 μg/dl iron.

Comparison study

Comparative assays were conducted using the Sera-Pak Iron kit and the present formulation. 25 human plasma heparin were used as samples.

Figure 5:
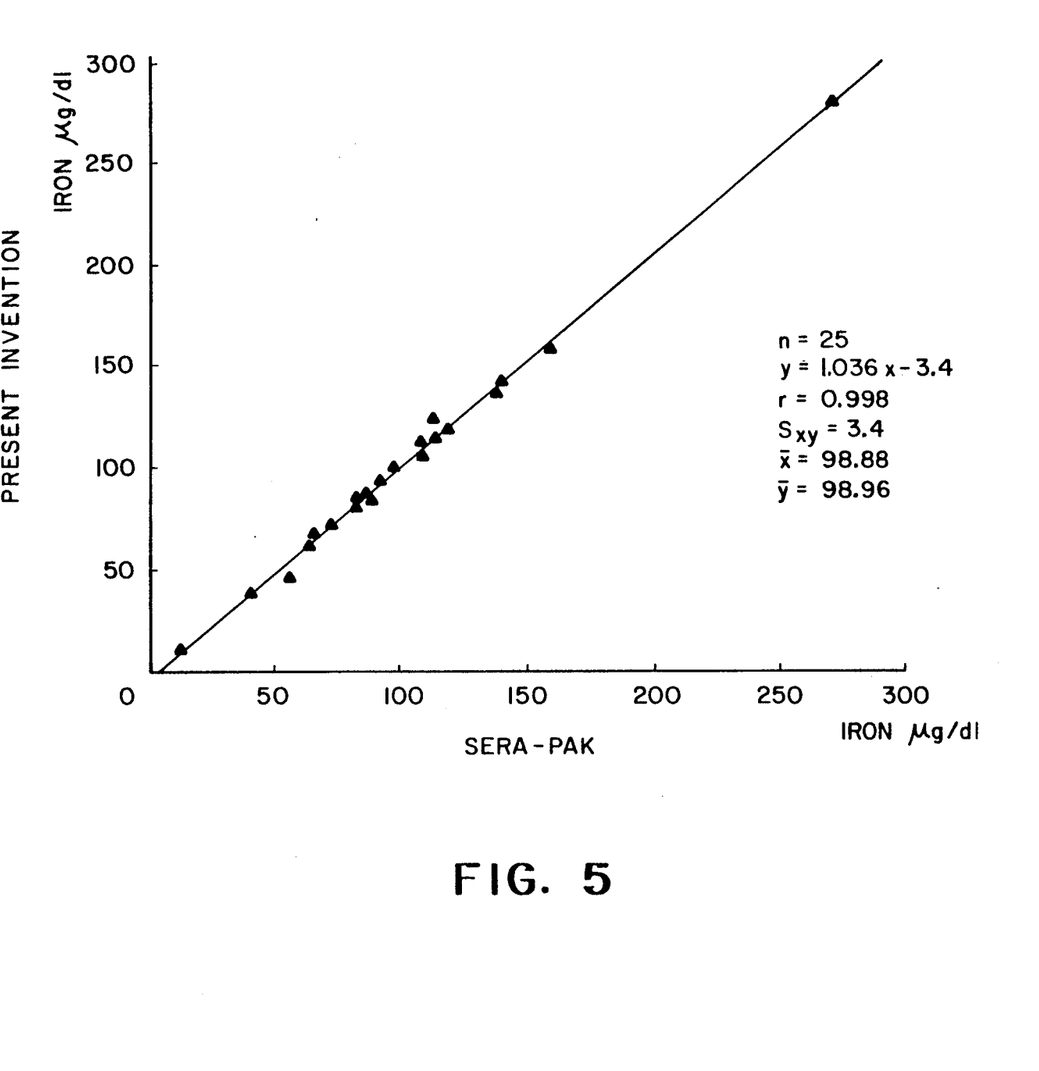
FIG. 5 shows a linear correlation between the Sera-Pak Iron test kit and the present formulation.

The results obtained, elaborated statistically by a linear method, are shown in FIG. 5. The correlation between the two methods is very good.

What is claimed is:

1. Compounds of the general formula (I)

wherein
$R^1$ denotes hydrogen, halogen or $C_1$-$C_4$ alkyl and
$R^2$ denotes $C_1$-$C_4$ alkyl, aryl or heteroalkyl or a substituted $C_1$-$C_4$ alkyl, aryl or heteroaryl.

2. Compounds of formula (I) according to claim 1 wherein
$R^1$ denotes hydrogen and
$R^2$ denotes $C_1$-$C_4$-alkyl, aryl or thienyl, which radicals can be substituted by $C_1$-$C_4$-alkyl, hydrogen, halogen or -$SO_3H$.

3. Compounds of formula (I) according to claim 1 wherein

$R^1$ denotes halogen and $R^2$ denotes methyl, ethyl, propyl, phenyl, tolyl or thienyl.

4. Compound of formula (I) according to claim 1 wherein $R^1$ denotes hydrogen and $R^2$ denotes wherein $R^{11}$ denotes hydrogen, methyl or chlorine.

5. Use of a compound according to claim 1 in the determination of iron in a biological fluid by reflectance method.

* * * * *